United States Patent [19]

Mahurkar

[11] Patent Number: 5,643,222

[45] Date of Patent: Jul. 1, 1997

[54] HYPODERMIC NEEDLE ASSEMBLY

[76] Inventor: Sakharam D. Mahurkar, 6171 N. Sheridan Rd., Suite 1112, Chicago, Ill. 60660

[21] Appl. No.: 494,283

[22] Filed: Jun. 23, 1995

Related U.S. Application Data

[60] Continuation-in-part of Ser. No. 229,811, Apr. 19, 1994, Pat. No. 5,514,100, which is a division of Ser. No. 111,372, Aug. 23, 1993, Pat. No. 5,338,311.

[51] Int. Cl.$^6$ ............................................. A61M 5/32
[52] U.S. Cl. ............................................. 604/195; 604/198
[58] Field of Search ............................................. 604/195, 110, 604/187, 192, 198, 263, 196

[56] References Cited

U.S. PATENT DOCUMENTS

| | | |
|---|---|---|
| 4,639,248 | 1/1987 | Schweblin . |
| 4,869,717 | 9/1989 | Adair . |
| 4,874,383 | 10/1989 | McNaughton . |
| 4,894,054 | 1/1990 | Miskinyar . |
| 4,921,489 | 5/1990 | Frizzell . |
| 4,935,013 | 6/1990 | Haber et al. . |
| 4,950,251 | 8/1990 | Haining . |
| 4,986,813 | 1/1991 | Blake, III et al. . |
| 4,994,034 | 2/1991 | Botich et al. . |
| 4,998,922 | 3/1991 | Kuracina et al. . |
| 5,000,167 | 3/1991 | Sunderland . |
| 5,114,404 | 5/1992 | Paxton et al. . |
| 5,147,324 | 9/1992 | Skakoon et al. . |
| 5,152,750 | 10/1992 | Haining . |
| 5,156,598 | 10/1992 | Skakoon et al. . |
| 5,176,640 | 1/1993 | Nacci et al. . |
| 5,190,526 | 3/1993 | Murray et al. . |
| 5,201,718 | 4/1993 | Whisson . |
| 5,205,823 | 4/1993 | Zdeb . |
| 5,209,739 | 5/1993 | Talalay . |
| 5,211,629 | 5/1993 | Pressly et al. . |
| 5,215,533 | 6/1993 | Robb . |
| 5,215,534 | 6/1993 | De Harde et al. . |
| 5,221,262 | 6/1993 | Kite . |
| 5,222,943 | 6/1993 | Mazzara . |
| 5,222,944 | 6/1993 | Harris . |
| 5,226,893 | 7/1993 | Kayser . |
| 5,232,456 | 8/1993 | Gonzalez . |
| 5,242,400 | 9/1993 | Blake, III et al. . |
| 5,246,428 | 9/1993 | Falknor . |
| 5,250,031 | 10/1993 | Kaplan et al. . |
| 5,254,099 | 10/1993 | Kuracina et al. . |
| 5,261,894 | 11/1993 | Smith et al. . |
| 5,267,961 | 12/1993 | Shaw . |
| 5,267,973 | 12/1993 | Haber et al. . |
| 5,267,976 | 12/1993 | Guerineau et al. . |
| 5,269,765 | 12/1993 | Kuracina . |
| 5,273,538 | 12/1993 | Chen . |
| 5,273,539 | 12/1993 | Chen . |
| 5,273,541 | 12/1993 | Malenchek . |
| 5,273,543 | 12/1993 | Bell et al. . |
| 5,279,582 | 1/1994 | Davison et al. . |
| 5,290,233 | 3/1994 | Campbell . |
| 5,295,975 | 3/1994 | Lockwood, Jr. . |
| 5,300,030 | 4/1994 | Crossman et al. . |
| 5,300,039 | 4/1994 | Poulsen . |
| 5,304,137 | 4/1994 | Fluke . |
| 5,304,149 | 4/1994 | Morigi . |
| 5,304,150 | 4/1994 | Duplan et al. . |
| 5,304,154 | 4/1994 | Gloyer et al. . |
| 5,312,347 | 5/1994 | Osborne et al. . |
| 5,312,365 | 5/1994 | Firth et al. . |
| 5,318,536 | 6/1994 | Williams . |
| 5,320,606 | 6/1994 | Jore . |
| 5,324,265 | 6/1994 | Murray et al. . |
| 5,336,186 | 8/1994 | Haber et al. . |
| 5,336,187 | 8/1994 | Terry et al. . |
| 5,336,197 | 8/1994 | Kuracina et al. . |
| 5,336,198 | 8/1994 | Silver et al. . |
| 5,338,304 | 8/1994 | Adams . |
| 5,342,323 | 8/1994 | Haining . |
| 5,344,403 | 9/1994 | Lee . |
| 5,352,208 | 10/1994 | Robinson . |
| 5,358,491 | 10/1994 | Johnson et al. ............ 604/195 X |
| 5,360,408 | 11/1994 | Vaillancourt . |
| 5,364,359 | 11/1994 | van den Haak . |
| 5,376,080 | 12/1994 | Petrussa . |
| 5,378,240 | 1/1995 | Curie et al. . |
| 5,380,286 | 1/1995 | van den Haak ............ 604/195 X |
| 5,380,297 | 1/1995 | Wadman et al. . |
| 5,385,555 | 1/1995 | Hausser . |
| 5,393,301 | 2/1995 | Goldberg . |
| 5,395,337 | 3/1995 | Clemens et al. . |
| 5,399,170 | 3/1995 | Whitley . |
| 5,403,286 | 4/1995 | Lockwood, Jr. . |

| | | |
|---|---|---|
| 5,407,431 | 4/1995 | Botich et al. . |
| 5,407,436 | 4/1995 | Toft et al. . |
| 5,415,645 | 5/1995 | Friend et al. . |
| 5,419,773 | 5/1995 | Rupp . |

*Primary Examiner*—John D. Yasko
*Attorney, Agent, or Firm*—Arnold, White & Durkee

[57] ABSTRACT

A needle-syringe assembly comprises an elongated, generally cylindrical barrel which forms a hollow nozzle located at the distal end of the barrel and which opens into the interior of the barrel. A plunger is slidably mounted in the barrel and forms a longitudinal cavity. A needle holder carries a hollow needle on the distal end, and the needle holder is slidably mounted in the longitudinal cavity of the plunger. The needle holder includes a lateral arm which extends between the plunger cavity and the barrel. A guide means forms a spiral guide surface which extends along a proximal end portion of the barrel for engaging the lateral arm of the needle holder and retracting the needle holder within the barrel in response to relative rotational movement between the barrel and the needle holder.

46 Claims, 10 Drawing Sheets

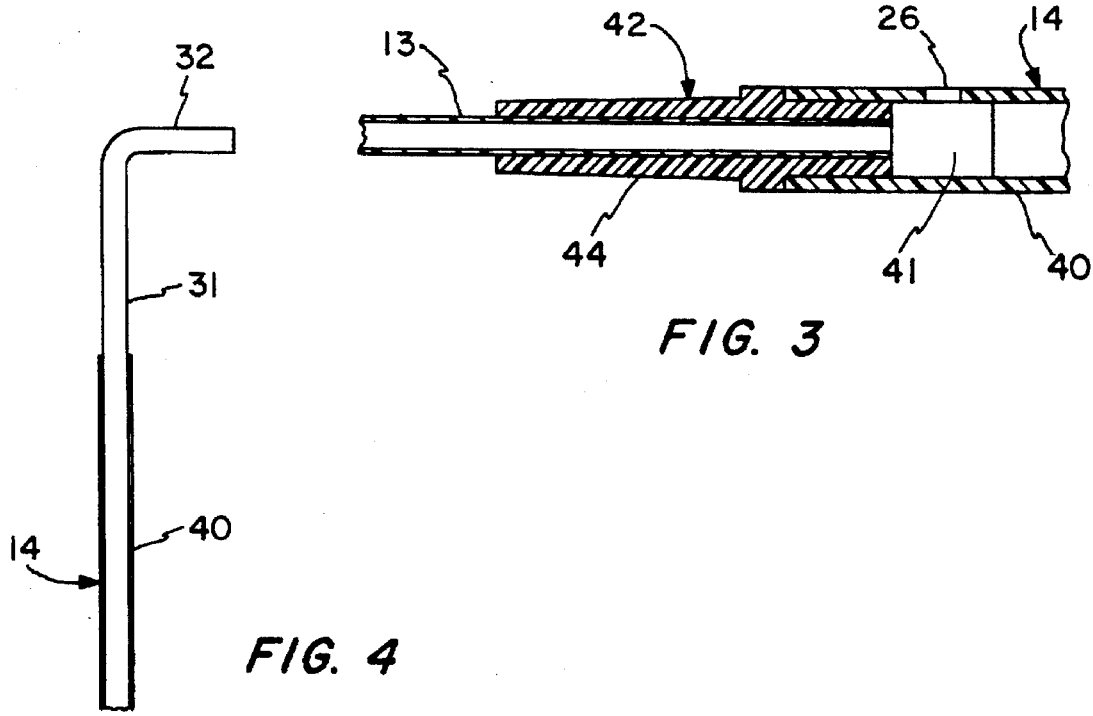
FIG. 3
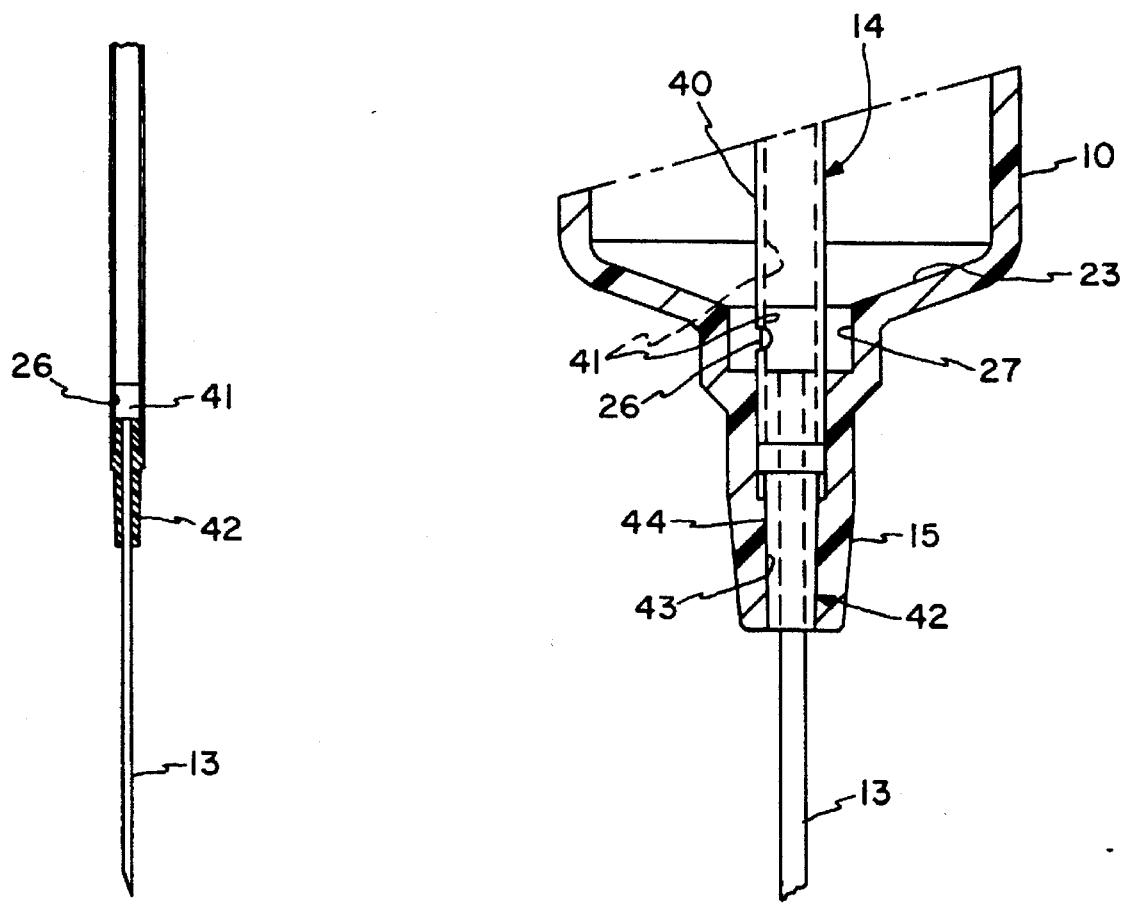
FIG. 4
FIG. 5

HYPODERMIC NEEDLE ASSEMBLY

CROSS-REFERENCES TO RELATED APPLICATIONS

This application is a continuation-in-part of U.S. patent application Ser. No. 229,811, filed Apr. 19, 1994, now U.S. Pat. No. 5,514,100 which in turn is a division of application Ser. No. 111,372, filed Aug. 23, 1993, now U.S. Pat. No. 5,338,311.

FIELD OF THE INVENTION

The present invention generally relates to hypodermic needles. In particular, the present invention relates to a needle-syringe assembly which conceals the sharp point of the hypodermic needle following use.

BACKGROUND OF THE INVENTION

A hypodermic needle has many applications in modern medicine. One application is to fit the hypodermic needle onto a syringe and to then insert the needle into a person's body for intra-muscular, subcutaneous, or intravenous injection of medications. A hypodermic needle entering into a patient's body is invariably contaminated by the patient's blood and body fluids. Following use of the needle, the needle presents a risk to physicians, nurses, and other health care personnel because the needle might transmit an infection or disease to such personnel if it were to accidently puncture them. Thus, health care personnel are in constant danger of contracting infections and diseases, some of which may be deadly. Other potential victims of accidental needle punctures include sanitation workers which later dispose of garbage containing the hypodermic needle. The diseases which may be transmitted by a contaminated hypodermic needle include Immune Deficiency Virus, Hepatitis, Rabies, Kure, Encephalitis, and Arbor viruses. The outcome of contracting one of these diseases is often fatal because there are no known cures for any of these diseases. Often a needle puncture in a person's skin is so trivial that it remains unrecognized until the person becomes seriously ill.

The problem of suffering accidental needle punctures is well recognized. As a result, enormous inventive effort has been devoted to concealing the sharp needle point of hypodermic needles. One such effort is described in the present applicant's U.S. Pat. No. 5,338,311, issued Aug. 16, 1994.

SUMMARY OF THE INVENTION

A primary object of the present invention is to improve the needle-syringe assembly described in the aforementioned U.S. Pat. No. 5,338,311.

One specific object of this invention is to provide an improved needle-syringe assembly which provides good structural stability for the mechanism that is used to retract the needle after it has been used.

Yet another object of the present invention is to provide such an improved needle-syringe assembly which facilitates fabrication, and reduces the cost, of the assembly.

Still another object of the present invention is to provide such an improved needle-syringe assembly which facilitates the operation of the assembly, particularly during retracting movement of the needle.

Another object of the present invention is to provide such an improved needle-syringe assembly which improves the acceptability of the assembly by providing an external appearance which is virtually the same as that of conventional hypodermic needle assemblies which do not provide for needle retraction.

A further object of the invention is to provide such an improved needle-syringe assembly that has the same length as conventional hypodermic needle assemblies which do not provide for needle retraction.

Other objects and advantages of the invention will become apparent upon reading the following detailed description and upon reference to the accompanying drawings.

In accordance with the present invention, the foregoing objectives are realized by providing a needle-syringe assembly, operable in a normal mode and convertible to a retraction mode, comprising an elongated, generally cylindrical barrel forming a hollow nozzle located at the distal end of the barrel and opening into the interior of the barrel; a plunger slidably mounted in the barrel and forming a longitudinal cavity extending between the distal end and the proximal end of the plunger; a needle holder carrying a hollow needle on the distal end thereof, the needle holder being slidably mounted in the longitudinal cavity of the plunger, the needle holder including a lateral arm extending between the plunger cavity and the barrel; and guide means forming a spiral guide surface extending along a proximal end portion of the barrel for receiving the lateral arm of the needle holder and retracting the needle holder within the barrel in response to relative rotational movement between the barrel and the plunger.

BRIEF DESCRIPTION OF THE DRAWINGS

FIG. 3 is an enlarged fragmentary longitudinal section through a distal portion of the needle holder of the needle-syringe assembly in FIG. 1;

FIG. 4 is an enlarged view of the needle and needle holder assembly shown in FIG. 1;

FIG. 5 is an enlarged fragmentary longitudinal section through a distal portion of the needle-syringe assembly in FIG. 2;

DETAILED DESCRIPTION OF THE PREFERRED EMBODIMENTS

Figure 1:
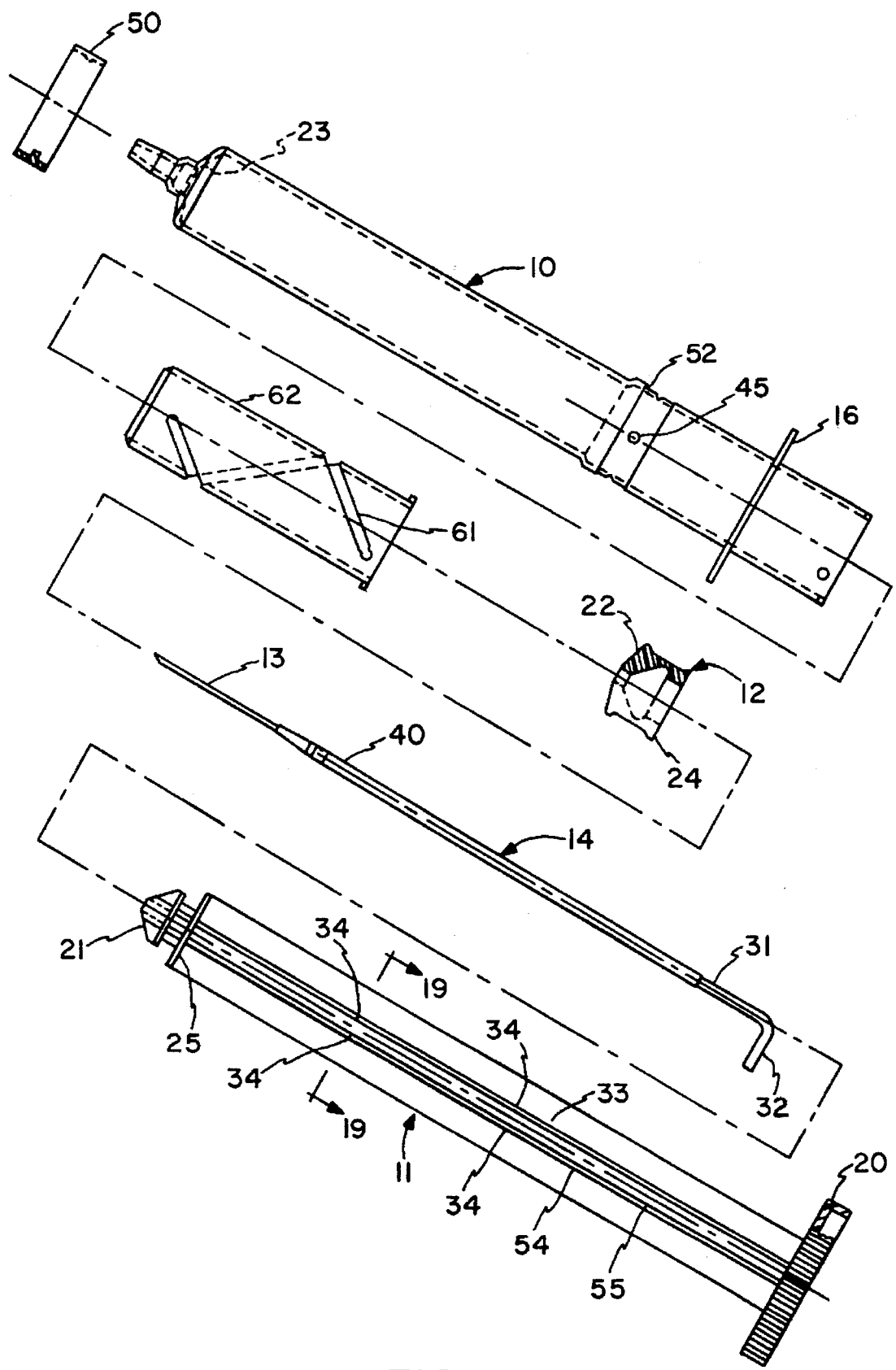
FIG. 1 is an exploded plan view of a needle-syringe assembly embodying the present invention.
Figure 2:
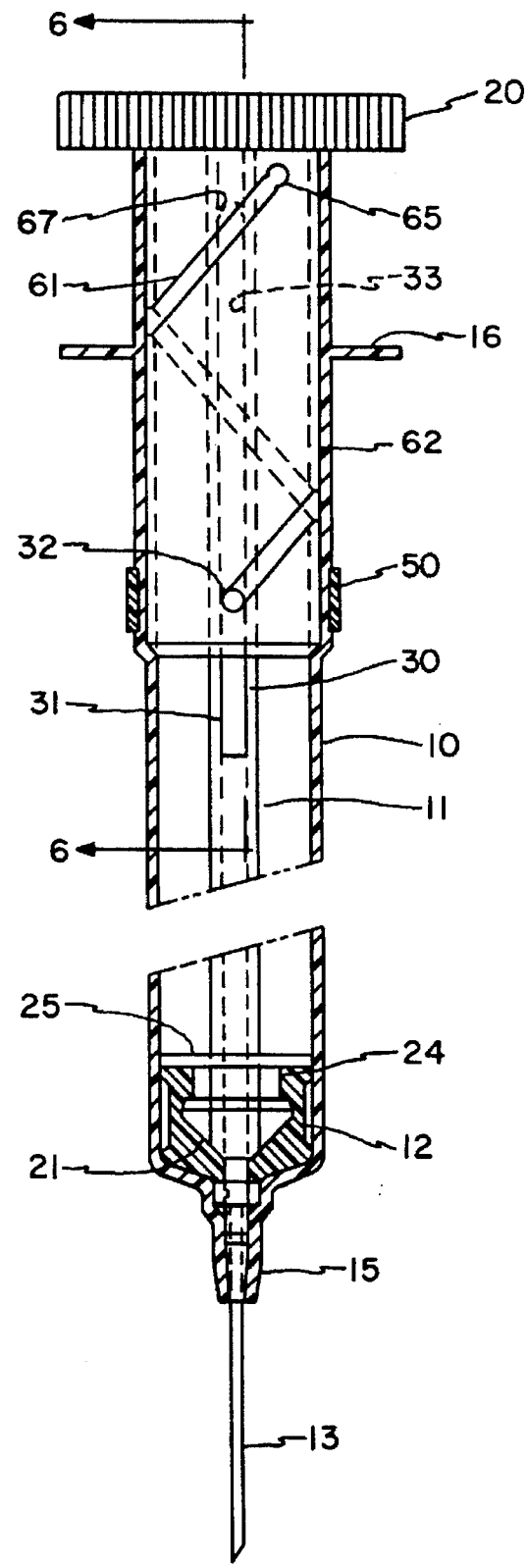
FIG. 2 is an enlarged longitudinal section of the needle-syringe assembly in FIG. 1 with the needle holder in the advanced position.

While the invention is susceptible to various modifications and alternative forms, specific embodiments thereof have been shown by way of example in the drawings and will herein be described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

Turning now to the drawings, FIGS. 1–12 illustrate a needle-syringe assembly including a barrel 10, a plunger 11, a hollow plunger cap 12, a hypodermic needle 13, and a needle holder 14. The barrel 10 is a hollow cylinder which terminates in a hollow tapered nozzle 15 at the distal end thereof, and has a slightly enlarged diameter along a proximal end portion. The interior of the nozzle 15 communicates with the hollow interior of the tubular body portion of the barrel 10. An outwardly extending flange 16 near the proximal end of the barrel 10 facilitates gripping of the barrel with the user's fingers when it is desired to move the plunger 11 relative to the barrel 10. The proximal end portion of the barrel 10 having the enlarged diameter provides a sufficient length to accommodate retraction of the needle holder 14 through a distance that is sufficient to draw the entire length of the needle 13 inside the barrel, as described in more detail below. The outer surface of the barrel 10 preferably contains graduations (not shown) indicating the volume level of fluid in the barrel. These graduations take into account the volume of the internal components such as the plunger 11 and the needle holder 14.

The proximal end of the plunger 11 forms a knob 20 that can be grasped by a user to permit linear or rotary movement of the plunger 11 relative to the barrel 10. The periphery of the knob 20 is serrated to facilitate gripping of the knob for rotary movements of the plunger. The distal end of the plunger 11 forms a head 21 to accommodate the hollow rubber plunger cap 12. The outside diameter of the resilient cap 12 is reduced in the central portion so that the cap engages the inside wall of the barrel 10 only at the pliable margins of the ends of the cap. The diameter of the engaging end portions of the cap is slightly larger than the inside diameter of the barrel 10 so that the cap presses firmly against the inside wall of the barrel to form an air-tight and liquid-tight seal at the cap/barrel interface. The inner margins of the cap make a similar tight contact with the outer surface of the needle holder. The distal end 22 of the cap 12 is conical to conform to the conical distal end 23 of the inside surface of the barrel 10 when the plunger 11 is fully advanced within the barrel.

The head 21 of the plunger 11 is configured to fit tightly within the hollow plunger cap 12. With the cap 12 locked onto the head 21 of the plunger, the flat proximal end 24 of the cap abuts the flat surface of a disc 25 at the base of the plunger head 21. Due to the air-tight and liquid-tight seal between the plunger cap 12 and the barrel 10, as well as the needle holder 14, advancing movement of the plunger 11 inside the barrel 10 creates pressure in the interior of the barrel between the plunger cap and the distal end of the barrel. Similarly, retracting movement of the plunger 11 creates a vacuum in that portion of the barrel interior.

The hypodermic needle 13 is mounted on the distal end of the elongated needle holder 14, which is detachably interlocked to the barrel 10. Prior to use of the needle-syringe assembly, the needle 13 is covered by a protective cap (not shown) which prevents needle pricks and preserves sterility prior to use. Both the needle 13 and the distal portion of the needle holder 14 are hollow, and the interior of the hollow needle 13 communicates with the interior of the hollow distal portion of the needle holder 14. The needle holder 14 further communicates with the interior of the barrel 10 through an aperture 26 in the side wall of the hollow portion of the needle holder 14 (FIGS. 3 and 5). Prior to and during use of the needle-syringe assembly for injection of medicine or withdrawal of blood (hereafter referred to as "normal use"), the aperture 26 is positioned within a small cylindrical cavity 27 at the base of the barrel nozzle (FIG. 5). The aperture 26 permits blood or medicine to enter or exit from the barrel 10 via the needle holder 14 and the needle 13.

During normal use of the needle-syringe assembly, the needle holder 14 is locked to the barrel 10, and the plunger 11 and its cap 12 are free to slide longitudinally back and forth along the needle holder. The needle holder 14 includes a metal tube 40 and an L-shaped metal rod 30 having a longitudinal body portion 31 extending coaxially through the tube 40 within the barrel 10, and a lateral arm 32 extending radially across the barrel.

To permit relative sliding movement between the plunger 11 and the needle holder 14 in the longitudinal direction, the needle holder is mounted in a longitudinal channel 33 formed as an integral part of the plunger 11. Multiple pairs of resilient retaining elements 34 (FIG. 1) project toward each other from the opposed walls of the channel 33 to hold the needle holder 14 within the channel. These retaining elements 34 are deflected into adjacent recesses 35 during insertion of the needle holder 14 into the channel 33, and then the elements 34 spring back to their original positions (FIG. 15) after the needle holder is in place. It will be noted that the opposed walls of the channel 33 extend all the way to the inside wall of the barrel 10 (see FIG. 7), thereby constraining the lateral arm 32 of the needle holder against any angular or rotational displacement relative to the plunger 11. That is, the plunger 11 and the needle holder 14 can rotate only in unison with each other, although they are free to move independently of each other in the longitudinal direction. At the proximal end of the needle holder a pair of locking detents (described below) lock the arm and plunger after retraction is complete.

A major portion of the stainless steel rod 30 is encased in a hypodermic stainless steel tube 40 which extends beyond the distal end of the rod 30 and overlaps a portion of the needle 13 (see FIGS. 3–5). The opposed ends of the needle 13 and the rod 30 are separated slightly from each other, and the intervening space is surrounded by the stainless steel tube 40 to form a cavity 41 through which fluids pass between the hollow interiors of the needle 13 and the barrel 10 (see FIGS. 3–5). The aperture 26 mentioned previously is formed in this portion of the tube 40.

The distal end of the tube 40 abuts a shoulder on a plastic insert 42 bonded to that portion of the needle that is within the barrel nozzle 15. This insert 42 fits tightly against the inside surface of the nozzle 15, and these mating surfaces of the insert 42 and the nozzle 15 are tapered to form a conventional locking luer taper (typically 6% of the diameter). Specifically, the inside surface of the nozzle 15 forms a locking female luer taper 43, and the outside surface of the insert 42 forms a locking male luer taper 44. In the preferred embodiment, the inside diameter of the nozzle 15 varies from 0.0737 inch at the proximal end of the taper to 0.0625 inch at the distal end of the taper. The longitudinal distance between these two inside diameters is 0.1875 inch. The diametric difference between the two diameters forms a taper in the nozzle 15 which is conventionally known as a locking female luer taper, and the angle formed by the diametric difference is conventionally known as a locking taper angle.

The locking surfaces 43 and 44 are engaged during assembly of the needle syringe, when the plunger 11 and needle holder 14 are inserted into the barrel 10 through the open distal end of the barrel. The resultant locking luer taper can be released only by the application of simultaneous axial and rotational forces. If desired, the tube 40 can be extended through the barrel nozzle and the taper formed on the distal end of the metal barrel rather on a plastic insert.

Figure 6:
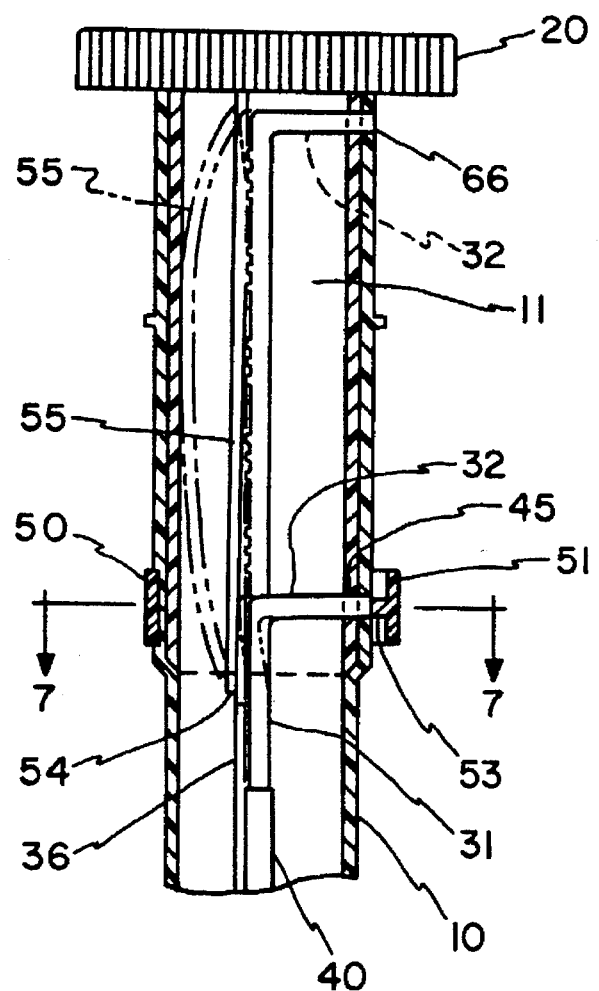
FIG. 6 is a section taken generally along line 6—6 in FIG. 2.
Figure 7:
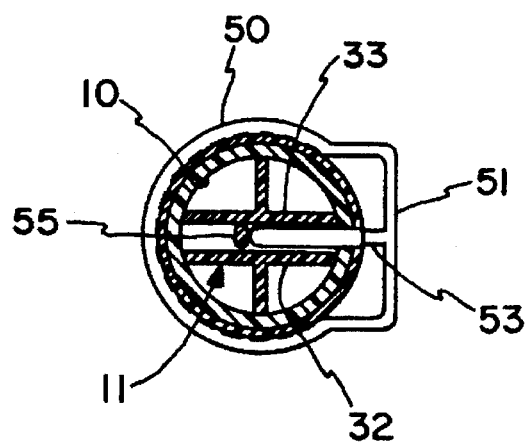
FIG. 7 is a section taken generally along line 7—7 in FIG. 6.

The proximal end of the needle holder 14 is also locked to the barrel 10, via the lateral arm 32 of the metal rod 30. As can be seen in FIGS. 6 and 7, this arm 32 extends radially beyond the plunger and fits into a latching hole 45 in the barrel wall. This locking engagement of the arm 32 with the barrel wall can be released only by moving the arm 32 in a radial direction until the outer end of the arm clears the inside surface of the barrel wall.

Figures 10, 11, 12:
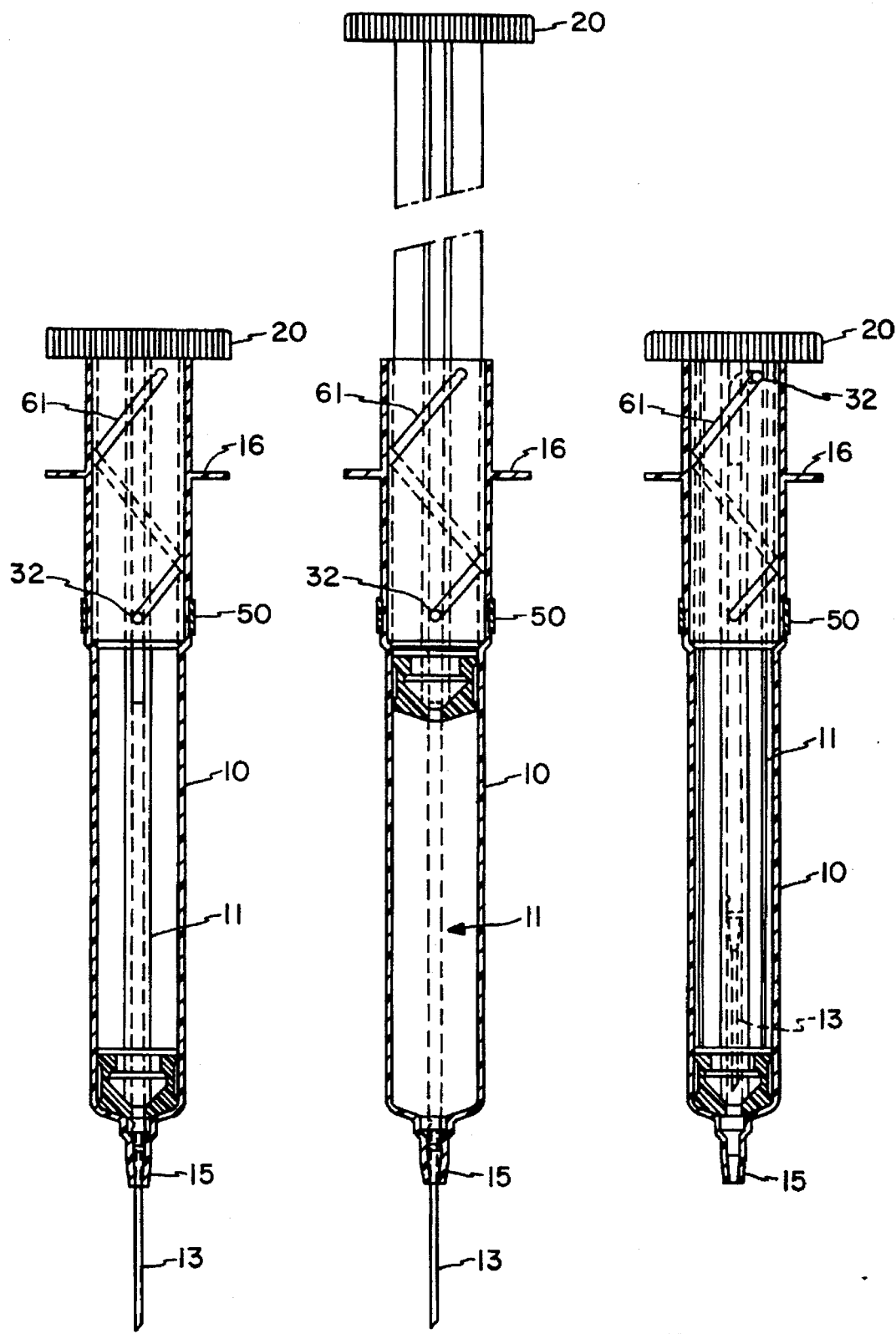
FIGS. 10 and 11 are longitudinal sections of the needle-syringe assembly of FIGS. 1–9 showing the available range of axial movement of the plunger relative to the barrel.
FIG. 12 is a longitudinal section of the needle-syringe assembly of FIGS. 1–11 with the needle holder in the retracted position and the needle concealed by the barrel.

During normal use of the needle-syringe assembly, the barrel 10 and the needle holder 14 are held stationary and the plunger 11 is free to move relative to both the barrel 10 and the needle holder 14 (see FIGS. 10 and 11). Advancing movement of the plunger 11 is limited by contact of the plunger cap 12 with the end wall 23 of the barrel 10, as shown in FIG. 10. Retracting movement of the plunger is limited by contact of the plunger cap 12 with the arm 32. The needle holder 14 is locked to the barrel 10 by virtue of the taper lock between the distal portion of the needle holder and the barrel nozzle 15, and the locking engagement of the lateral arm 32 in the wall of the barrel. Alternatively, the needle holder can be locked to the nozzle by a threaded connection, as described in more detail below. The plunger 11 is also free to move longitudinally relative to the needle holder 14, as illustrated in FIG. 11, because the needle holder is not locked to the plunger in that direction. The locking of the lateral arm 32 to the barrel wall prevents rotational movement of the plunger as well as the needle holder, and also prevents the plunger from being accidentally pulled out. As long as the lateral arm 32 of the needle holder is engaged with the barrel wall, the needle-syringe assembly is in its normal operating mode.

Following normal use of the needle-syringe assembly, the entire needle 13 can be retracted into the plunger 11 and the barrel 10. This requires axial movement of the needle holder 14 within the barrel 10 toward the proximal end thereof, which in turn requires that the needle holder 14 be unlocked from the barrel. Thus, to initiate retraction of the needle holder 14, the arm 32 is unlatched from the barrel 10 by pressing inwardly on a flat portion 51 of a resilient collar 50 captured in a groove 52 in the outer surface of the barrel. This causes a radial pin 53 extending inwardly from the flat portion 51 to enter the latching hole 45 in the barrel wall, engaging the outer end of the arm 32 and forcing it inwardly (see FIGS. 6 and 7). This can also be done by pushing directly on the end of the arm with the user's finger, if a concave depression is formed around the latching hole 45, as described in more detail below. This inward force causes the body of the needle holder adjacent the arm 32 to retract, as illustrated in FIG. 6, which in turn moves the arm 32 inwardly far enough to clear the inner surface of the barrel wall. If desired, the opposed surfaces of the collar 50 and the barrel 10 may be provided with mating projections and recesses to hold the collar on the barrel, and the collar may even be adhesively bonded to the barrel.

To enable the rod 31 to disengage by moving laterally, the narrow wall 36 which forms the base of the channel 33 is cut transversely at 54 and then slit longitudinally along both edges from the cut 54 to a point just slightly spaced from the knob 20 (see FIG. 1). This transverse cut 54 and the longitudinal slits form a spring finger 55 which bears against the proximal end of the longitudinal portion of the rod 31 at all times, while permitting the rod 31 to be displaced laterally or transversely within the barrel 10.

While the flat portion of the collar 50 is pressed inwardly against the barrel 10 to release the arm 32 from the barrel wall, the plunger knob 20 is turned to rotate the plunger 11 counterclockwise (as viewed from the proximal end) relative to the barrel. As the plunger is rotated, the needle holder 14 rotates in unison with the plunger because the arm 32 is captured between the opposed parallel walls of the channel 32 in which the needle holder is mounted in the plunger. Rotation of the needle holder 14 relative to the barrel (1) retracts the needle holder within the plunger by the camming action of a spiral guide surface 60 acting on the arm 32, and (2) releases the locking luer taper at the distal end of the barrel nozzle 15 due to the resulting compound rotational and longitudinal forces applied to the tapered surfaces 43 and 44. As rotation continues, the arm 32 traverses the entire length of the spiral surface 60, thereby retracting the entire needle holder 14 through a corresponding axial distance within the plunger 11 (see FIG. 12). Of course, the needle 13 is retracted along with the needle holder 14, and thus the needle is retracted completely within the barrel nozzle 10 and the plunger 11, as illustrated in FIG. 12.

Figure 8:
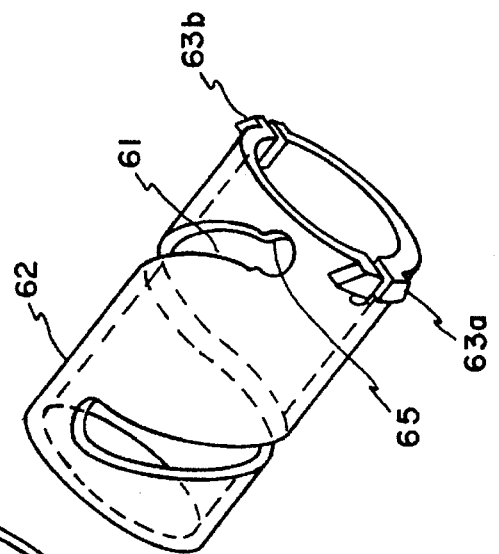
FIG. 8 is an enlarged exploded perspective view of the proximal end portion of the barrel of the needle-syringe assembly of FIGS. 1–7.
Figure 9B:
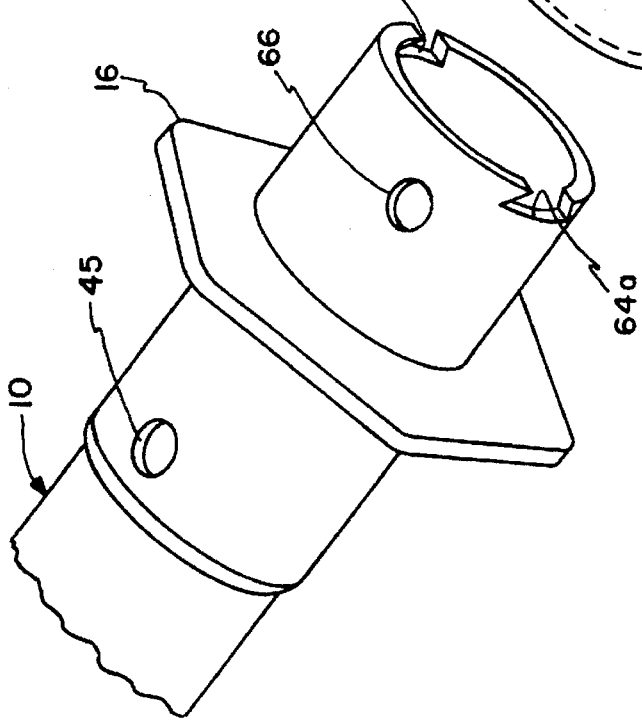
FIG. 9b is a side elevation of the proximal end of the barrel shown in FIG. 8.
Figure 9B:
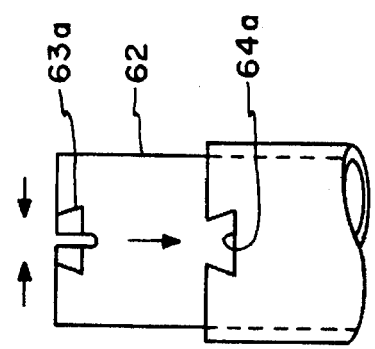

In the illustrative embodiment, the spiral guide surface 60 is formed by a spiral slot 61 in a sleeve 62 fitted inside a distal end portion of the barrel 10, and attached to the barrel. The illustration of the slot 61 is simplified in most of the drawings by the use of straight lines, but it will be understood that the spiral slot has a constant rate of curvature, as shown in FIG. 8. The portion of the barrel 10 that receives the sleeve 62 has a slightly larger diameter than the central portion of the barrel, and the sleeve 62 has the same inside diameter as the central portion of the barrel. Alternatively, a spiral channel can be molded as a part of the inside wall of the end portion of the barrel that has the slightly larger diameter. The illustrative syringe need not be any longer than a conventional syringe because conventional syringes are made longer than required to provide the desired fluid volume, to avoid inadvertent withdrawal of the plunger and the resultant spillage of the syringe contents. The extra barrel length also accommodates the user's fingers in the space between the plunger knob and the finger flanges. The present invention permits the interior of this extra barrel length to be used for the needle-retracting mechanism.

To attach the sleeve 62 to the barrel 10, a pair of tabs 63a, 63b extend outwardly from opposite sides of the sleeve 62 into a pair of complementary notches 64a, 64b in the distal end of the barrel. To lock the sleeve to the barrel longitudinally as well as rotationally, the tabs 63 and notches 64 have complementary dovetail shapes. Each tab is bifurcated by a central slot so that the tapered sides of the tab can be displaced toward each other during insertion of the tabs into the notches. Then when the tabs 63 resume their original shapes after being inserted into the notches 64, the two parts are securely locked together in both the longitudinal and circumferential directions.

Figure 9A:
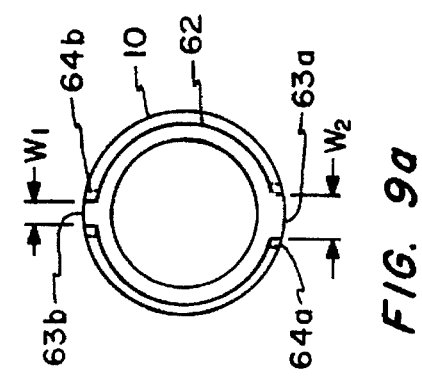
FIG. 9a is an end elevation of the barrel shown in FIG. 8.

To ensure that the spiral slot 61 in the sleeve 62 is always properly aligned with the locking holes in the barrel 10, the two tabs 63a, 63b and the two notches 64a, 64b have different widths, as can be seen in FIG. 9a. Thus, the locking hole 45 in the barrel 10 will always be aligned with the distal end of the spiral slot 61. The same effect may be achieved with the use of asymmetrical tabs of equal width.

Because the distal end of the spiral slot 61 is precisely registered with the latching hole 45 in the barrel wall, the arm 32 can pass through the slot 61 to gain access to the latching hole. When the arm 32 is disengaged from the latching hole 45, by manipulation of the collar 50 as described above, the arm still passes through the spiral slot 61, but the outer end of the arm now rides on the inside surface of the wall of the barrel 10 as the arm is cammed along the slot (see FIG. 6). The longitudinal portion of the rod 31 remains against the spring finger 55 during this movement of the arm 32 along the spiral slot 61. The retraction length is equal to the linear length of the spiral between the centers of the two holes 45 and 66.

At the distal end of the spiral slot 61, the end of the arm 32 snaps into a detent notch 65 (FIGS. 2 and 8) formed by the walls of the slot so that the user feels the end of the needle retraction. At the same time, the outer end of the arm 32 enters a locking aperture 66 in the barrel wall. The arm 32 is forced into the locking aperture 66 by the inherent spring force of the rod itself, as well as the force of the spring finger 55, which increases toward the base of that finger. Then if the user attempts to turn the plunger knob 20 in the opposite direction, such attempt is met with firm resistance. This is a safety feature to prevent the needle from being returned beyond the end of the barrel nozzle, and to discourage re-use of the needle.

A pair of resilient locking fingers 67 are formed in the opposed walls of the channel 33 near the proximal end thereof to prevent the plunger from being withdrawn from the barrel 10 after the needle holder has been retracted. The arm 32 deflects the fingers 67 into adjacent recesses as the arm is retracted past the fingers, but the arm 32 then blocks any effort to retract the plunger over the needle holder.

To operate the needle-syringe assembly, the protective cap is removed from the needle 13, and the required amount of medication is aspirated into the barrel 10. Next, the injection site on the body of a patient is determined and the skin is cleaned with an antiseptic solution. Following percutaneous entry of the needle into the patient, location of the needle tip in the vein is confirmed by aspirating a small amount of blood into the transparent barrel 10. The plunger 11 is then advanced to force the medication from the barrel 10 into the vein. After the medication is administered, the needle 13 is withdrawn from the patient, the flat portion 51 of the collar 50 is pressed inwardly against the barrel 10, and the plunger knob 20 is rotated counterclockwise until the user feels the arm 32 snap into the locking aperture 66 and the detent 65 at the end of the spiral slot 61. The spiral slot 61 may alternatively be configured to require clockwise, instead of counterclockwise, rotation of the plunger knob 20. With the needle 13 completely retracted inside the barrel 10, the needle-syringe assembly can be safely discarded in its entirety.

It can be seen from the foregoing description that the needle-syringe assembly performs all the conventional functions of injection syringes and yet, upon completion of injection, the hypodermic needle 13 is concealed within the barrel 10. The needle-syringe assembly can receive and inject medications any number of times into a particular patient by reciprocal longitudinal movement of the plunger 11 within the barrel 10. Another advantage of the needle-syringe assembly is that its design prevents the plunger 11 from slipping out of the barrel 10 during normal use of the assembly.

The needle-syringe assembly of this invention is easy to manufacture, cost-effective, and easy to use in the field. The parts can all be made by conventional plastic molding or from readily available metal stock. The assembly is compact because the needle holder 14 is retracted directly into the plunger 11 itself and thus the plunger 11 need not be fully extended for needle retraction to occur. When discarded following use, the needle-syringe assembly contributes minimally to the bulk of refuse. Since retraction of the needle 13 is effected by turning the plunger knob 20 at the proximal end of the assembly, the hand of a user does not come into the vicinity of the needle point, thereby minimizing the possibility of a needle prick during retraction. Moreover, the assembly employs substantially the same number of components as conventional syringes, and does not require additional guards, sheaths, sleeves, springs, etc. to conceal the needle following use.

Figure 13:
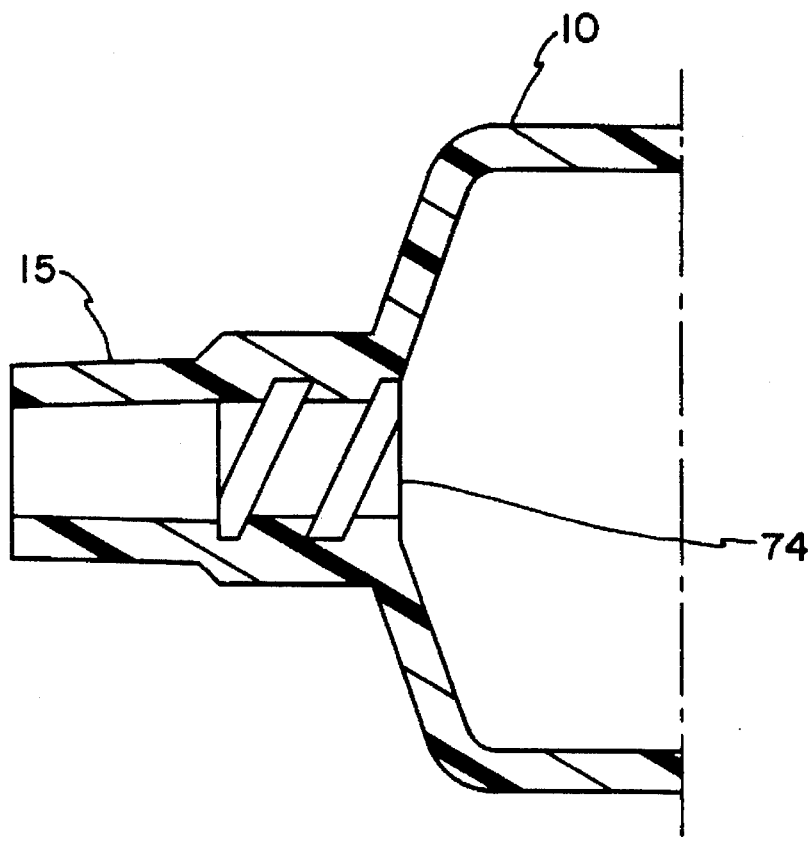
FIG. 13 is a longitudinal section similar to FIG. 5 but showing a modified construction of the barrel nozzle.
Figure 14:
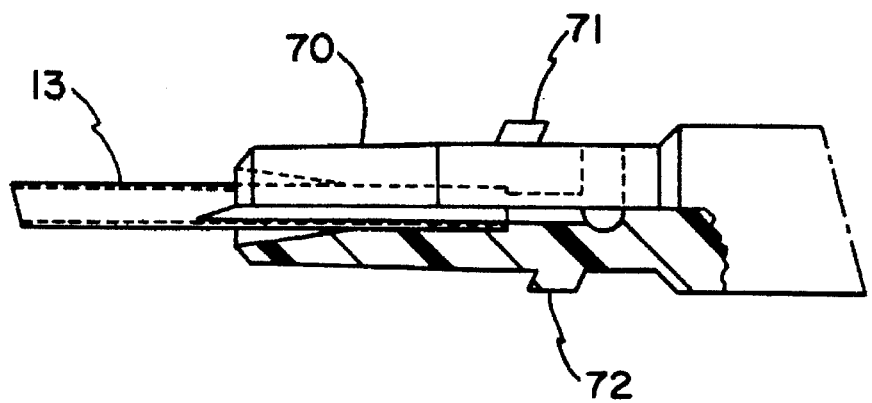
FIG. 14 is an enlarged side elevation, partially in section, of a modified needle holder for use with the barrel nozzle shown in FIG. 13.

FIGS. 13 and 14 illustrate a modified construction for locking the distal end of the needle holder 14 to the barrel nozzle 15. In this design the plastic insert 42 is modified to form a pair of integral lugs 71 and 72 which thread into a threaded inside surface 73 in the barrel nozzle 15. When the plunger 11 is inserted into the barrel 10 and advanced to the distal end of the barrel, the distal end of the needle holder 14 carried in the plunger enters the nozzle 15. The plunger is automatically rotated by the advancing movement of the arm 32 through the spiral slot 61, and thus the lugs 71,72 are automatically threaded into the nozzle 15. Similarly, when the needle is subsequently retracted, the retracting movement of the arm 32 through the spiral slot 61, and the consequent rotation of the needle holder 14, threads the lugs 71,72 out of the barrel nozzle.

Figure 15:
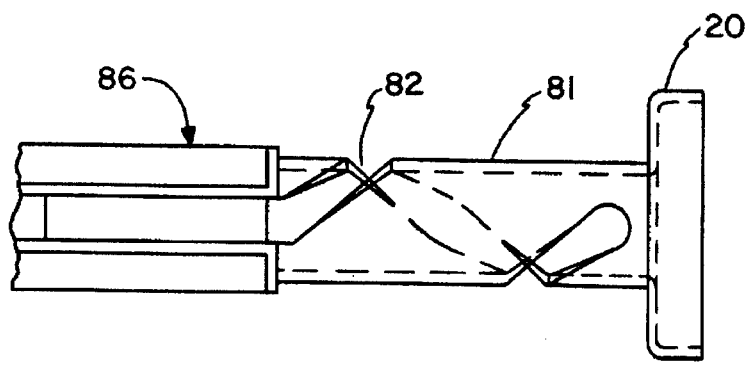
FIG. 15 is a side elevation of the proximal end portion of a modified needle-syringe assembly embodying the invention.
Figure 16:
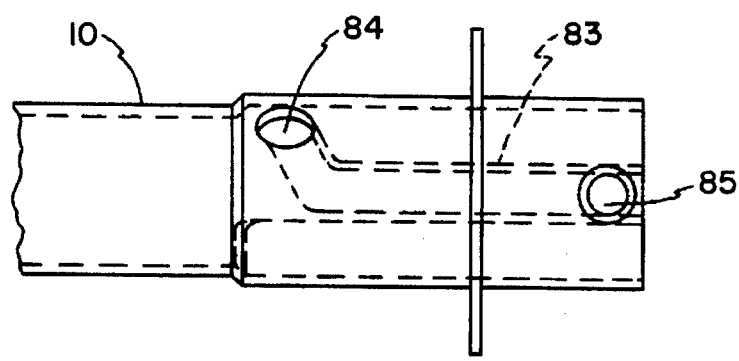
FIG. 16 is a side elevation of the proximal end portion of a barrel for use with the plunger of FIG. 15.
Figure 17:
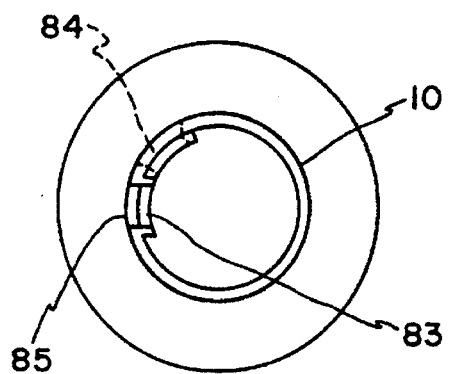
FIG. 17 is an end elevation of the assembly shown in FIG. 16.

FIGS. 15–17 illustrate a modified plunger and barrel design in which the spiral guide surface is formed by the plunger rather than the barrel. Thus, the proximal end of the plunger 80 includes a hollow cylindrical section 81 adjacent the knob 20, and the wall of this section forms a spiral slot 82. The needle holder arm 32 extends radially outwardly through the slot 82 and into a generally linear channel 83 in the adjacent wall of the barrel 10. Latching holes 84 and 85 are formed in the barrel wall at opposite ends of the channel 83. When the arm 32 is released from the forward latching hole 82, the plunger is turned to move the end of the arm 32 into the channel 83. The arm 32 moves through the hole 82 until it engages the side of the longitudinal section of the channel 83, which then permits longitudinal but not rotational movement of the needle holder as the plunger continues to be turned. Thus, the spiral slot 82 in the plunger acts as a camming surface to urge the arm 32 along the channel 83, thereby retracting the needle 13 into the barrel 10 and ultimately locking it to the barrel margin as described for the first embodiment.

Figure 18:
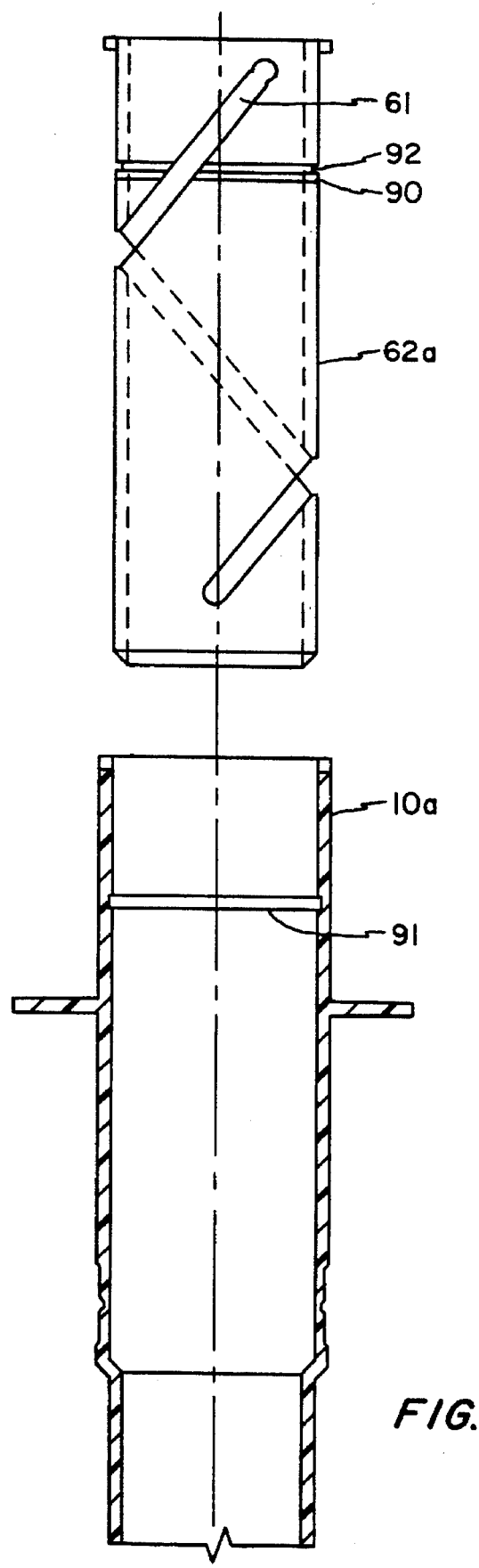
FIG. 18 is an exploded side elevation of the proximal end portion of a modified barrel construction.
Figure 19:
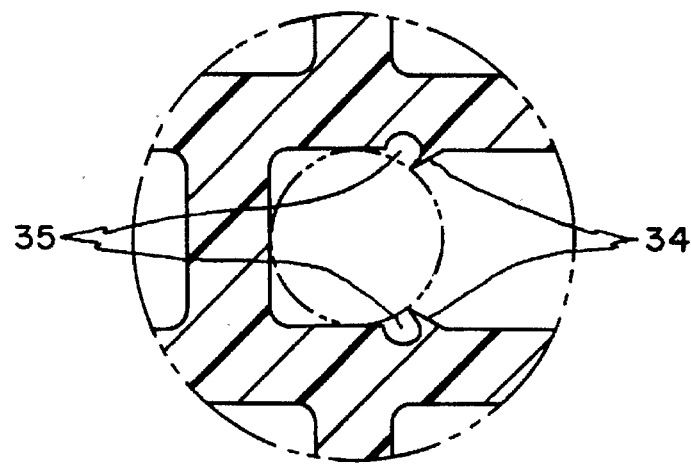
FIG. 19 is an enlarged section taken along line 19—19 in FIG. 1.

FIG. 18 illustrates a modified design for locking the barrel 62 to the barrel 10. In this case the outside wall of the barrel sleeve 62a forms a resilient lip 90 which snaps into a complementary groove 91 in the inside wall of the barrel body 10a. During sliding movement of the sleeve 62a through the barrel 10a, the lip 90 is bent into an adjoining groove 92 in the sleeve. The interlocking of the lip 90 and the groove 91 prevent relative longitudinal movement between the sleeve and the barrel. A locking tab, of the type described above, can be provided to lock the two members against rotational movement.

Figure 20:
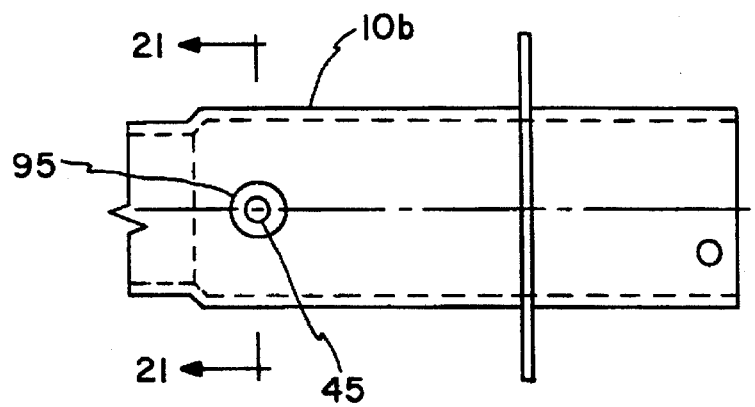
FIG. 20 is a side elevation of the proximal end portion of a modified barrel design.
Figure 21:
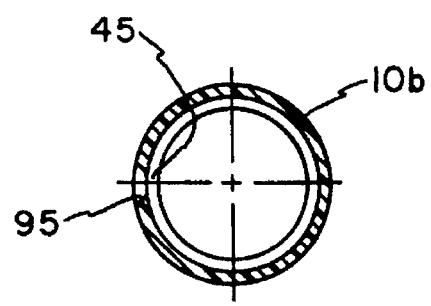
FIG. 21 is a section taken along line 21—21 in FIG. 20.

FIGS. 20 and 21 show a modified design for the proximal end of the barrel 10. This modified barrel 10b eliminates the need for the collar 50 by providing a circular depression around the latching hole 45. This depression 95 allows a user's finger to engage the end of the lateral arm 32 and to press the arm inwardly to disengage it from the latching hole 45. The plunger is then turned relative to the barrel while the arm 32 is pressed inwardly, to initiate the retracting movement of the needle holder.

What is claimed is:

1. A needle-syringe assembly, comprising:
   an elongated, generally cylindrical barrel forming a hollow nozzle located at the distal end of said barrel and opening into the interior of said barrel;
   a plunger slidably mounted in said barrel and forming a longitudinal cavity;
   a needle holder carrying a hollow needle on the distal end thereof, said needle holder being slidably mounted in said longitudinal cavity of said plunger, said needle holder including a lateral arm extending laterally through said plunger cavity to said barrel; and
   guide means forming a spiral guide surface extending along a proximal end portion of said barrel for engaging the lateral arm of the needle holder and retracting the needle holder within the barrel in response to relative rotational movement between the barrel and the needle holder.

2. The needle-syringe assembly of claim 1 wherein said guide means comprises a sleeve disposed inside the proximal end portion of the barrel and fixed to the barrel.

3. The needle-syringe assembly of claim 2 wherein said spiral guide surface is formed by a spiral slot in said sleeve.

4. The needle-syringe assembly of claim 1 which includes means for preventing rotation of said needle holder relative to said plunger so that the needle holder and plunger must rotate in unison.

5. The needle-syringe assembly of claim 1 wherein the lengths of the barrel and the needle holder are selected such that the needle attached to the distal end of the needle holder is fully retracted within the barrel when the lateral arm of the needle holder is retracted to the proximal end of the spiral guide surface.

6. The needle-syringe assembly of claim 1 which includes latching means for releasably latching the needle holder to the barrel when the needle holder is in its fully advanced position.

7. The needle-syringe assembly of claim 6 wherein said latching means comprises a latching hole in the wall of the barrel for receiving the outer end of the lateral arm of the needle holder to latch the needle holder to the barrel, and manually actuatable means for moving the lateral arm inwardly to unlatch the needle holder from the barrel.

8. The needle-syringe assembly of claim 7 wherein a portion of the needle holder adjacent the lateral arm is movable laterally by an amount sufficient to release the outer end of the lateral arm from the latching hole in the barrel wall.

9. The needle-syringe assembly of claim 8 wherein the needle-holder cavity in the plunger has a flexible wall to permit lateral disengaging movement of said arm.

10. The needle-syringe assembly of claim 7 wherein the manually actuatable means is a collar captured on the outer surface of the barrel and forming an inwardly extending pin registered with the latching hole in the barrel wall, the portion of the collar adjacent the pin being resilient to enable the pin to be advanced into the latching hole to force the lateral arm of the needle holder out of the latching hole.

11. The needle-syringe assembly of claim 1 wherein said longitudinal cavity is a channel formed as an integral part of the plunger.

12. The needle-syringe assembly of claim 11 wherein the opposed walls of said channel engage opposite sides of the lateral arm of the needle holder to prevent the needle holder from rotating relative to the plunger.

13. The needle-syringe assembly of claim 12 wherein the locking male luer taper is formed by a polymeric sleeve molded on a proximal extension of the hollow needle.

14. The needle-syringe assembly of claim 1 wherein the distal portion of the inside surface of the hollow nozzle on the barrel forms a locking female luer taper, and a distal portion of the outside surface of the needle holder forms a locking male luer taper.

15. The needle-syringe assembly of claim 1 wherein mating surfaces of the distal portions of the hollow nozzle on the barrel and the needle holder form cooperating threads for locking the needle holder to the barrel during longitudinal movement of the plunger relative to the barrel.

16. The needle-syringe assembly of claim 15 wherein the threads on said needle holder are formed by a polymeric sleeve molded on a proximal extension of the hollow needle.

17. The needle-syringe assembly of claim 1 wherein said spiral guide surface includes a locking detent at the proximal end thereof, to resist advancing movement of the needle holder after it has been fully retracted.

18. The needle-syringe assembly of claim 1 wherein said guide means is formed by a proximal end portion of the plunger.

19. The needle-syringe assembly of claim 18 wherein the proximal end portion of the plunger is a hollow cylinder, and said guide means is a spiral slot in said hollow cylinder.

20. The needle-syringe assembly of claim 18 wherein the proximal end portion of said barrel forms a longitudinal channel receiving said lateral arm of said needle holder for preventing rotation of said arm while permitting longitudinal movement thereof.

21. The needle-syringe assembly of claim 6 wherein said latching means comprises a latching hole in the wall of the barrel for receiving the outer end of the lateral arm of the needle holder to latch the needle holder to the barrel, and the outside surface of the barrel forms a depression around said latching hole to permit a finger to engage the end of said lateral arm and move the arm inwardly to disengage the arm from the barrel.

22. The needle-syringe assembly of claim 1 which includes locking means for locking the needle holder to the barrel in response to movement of the needle holder to its retracted position.

23. The needle-syringe assembly of claim 22 which includes second locking means for locking the plunger to the needle holder in response to movement of the needle holder to its retracted position.

24. A needle-syringe assembly, comprising:
   an elongated, generally cylindrical barrel forming a hollow nozzle located at the distal end of said barrel and opening into the interior of said barrel;

a plunger slidably mounted in said barrel and forming a longitudinal cavity;

a needle holder carrying a hollow needle on the distal end thereof, said needle holder being slidably mounted in said longitudinal cavity of said plunger, said needle holder including a lateral arm extending laterally through said plunger cavity to said barrel;

guide means forming a spiral guide surface extending along a proximal end portion of said barrel for engaging the lateral arm of the needle holder and retracting the needle holder within the barrel in response to relative rotational movement between the barrel and the needle holder;

means for preventing rotation of said needle holder relative to said plunger so that the needle holder and plunger must rotate in unison; and the lengths of the barrel and the needle holder are selected such that the needle attached to the distal end of the needle holder is fully retracted within the barrel when the lateral arm of the needle holder is retracted to the proximal end of the spiral guide surface.

25. A needle-syringe assembly, comprising:

an elongated, generally cylindrical barrel forming a hollow nozzle located at the distal end of said barrel and opening into the interior of said barrel;

a plunger slidably mounted in said barrel and forming a longitudinal cavity;

a resilient cap mounted on the distal end of said plunger and forming a sliding seal on the inside surface of the barrel;

a needle holder carrying a hollow needle on the distal end thereof, said needle holder being slidably mounted in said longitudinal cavity of said plunger and extending through the resilient cap on the distal end of the plunger, said cap forming a sliding seal on the outside surface of the needle holder;

said needle holder including a lateral arm that simultaneously engages said barrel and said plunger;

said needle holder also extending into the nozzle of said barrel, the mating surfaces of the needle holder and the barrel nozzle forming a locking taper; and guide means along a proximal end portion of said barrel for engaging the lateral arm of said needle holder and retracting the needle holder within said barrel in response to relative rotational movement between the barrel and the needle holder.

26. The needle-syringe assembly of claim 25 wherein said guide means includes a sleeve inserted in the proximal end of the barrel, and said sleeve is fixed to said barrel by means of a plurality of complementary notches and tabs.

27. The needle-syringe assembly of claim 26 wherein said complementary notches and tabs have dovetail shapes.

28. The needle-syringe assembly of claim 25 wherein said needle holder includes a fluid cavity communicating with the interiors of the barrel and of the hollow needle mounted on the distal end of the needle holder.

29. The needle-syringe assembly of claim 25 wherein said barrel includes a latching hole for receiving the end of said arm, and the outer surface of the barrel forms a depression around said latching hole to permit the outer end of the lateral arm to be engaged by a finger and moved inwardly to disengage the arm from the latching hole in the barrel wall.

30. The needle-syringe assembly of claim 25 wherein said longitudinal cavity includes a channel receiving the plunger, and said channel includes multiple pairs of resilient retaining elements to hold said needle holder within said channel.

31. The needle syringe-assembly of claim 25 wherein said locking taper is releasable by the application of simultaneous axial and rotational forces.

32. The needle-syringe assembly of claim 25 wherein said needle is a hypodermic needle.

33. A needle-syringe assembly, comprising:

an elongated, generally cylindrical barrel forming a hollow nozzle located at the distal end of said barrel and opening into the interior of said barrel;

a plunger slidably mounted in said barrel and forming a longitudinal cavity;

a needle holder carrying a hollow hypodermic needle on the distal end thereof, said needle holder being slidably mounted in said longitudinal cavity of said plunger, said needle holder including a lateral arm extending laterally through said longitudinal cavity of said plunger to said barrel;

said longitudinal cavity forming a channel that engages opposite sides of said lateral arm of the needle holder to prevent the needle holder from rotating relative to the plunger;

guide means forming a spiral guide surface extending along a proximal end portion of said barrel for engaging the lateral arm of the needle holder and retracting the needle holder within the barrel in response to relative rotational movement between the barrel and the needle holder, said guide means comprising a sleeve with a spiral slot disposed inside the proximal end portion of the barrel and fixed to the barrel;

first locking means for securing the needle holder to the barrel when the needle holder is in its advanced position;

second locking means for securing the needle holder to the barrel when the needle holder is in its retracted position; and third locking means for securing the plunger to the needle holder when the needle holder is in its retracted position.

34. The needle-syringe assembly of claim 33 wherein said guide means includes a sleeve inserted in the proximal end of the barrel, and said sleeve is fixed to said barrel by means of a plurality of complementary notches and tabs.

35. The needle-syringe assembly of claim 34 wherein said complementary notches and tabs have dovetail shapes.

36. The needle-syringe assembly of claim 33 wherein said needle holder includes a fluid cavity communicating with the interiors of the barrel and of the hollow needle mounted on the distal end of the needle holder.

37. The needle-syringe assembly of claim 33 wherein said first locking means includes a latching hole in the wall of the barrel for receiving the end of said arm, and the outer surface of the barrel forms a depression around said latching hole to permit the outer end of the lateral arm to be engaged by a finger and moved inwardly to disengage the arm from the latching hole in the barrel wall.

38. The needle-syringe assembly of claim 33 wherein said longitudinal cavity includes a channel receiving the plunger, and said channel includes multiple pairs of resilient retaining elements to hold said needle holder within said channel.

39. A needle-syringe assembly comprising a barrel, a plunger within the barrel for sliding longitudinal movement and rotational movement relative to the barrel, and a needle holder within the plunger for sliding longitudinal movement relative to the plunger, said needle holder being moveable beyond the distal end of said plunger for advancing a needle through and beyond the distal end of said barrel, sealing means at the distal end of the needle holder for sealing the interface between the barrel and the needle holder against fluid flow when the needle holder is in its most distal position, means for retracting said needle holder within said barrel, and latch means for selectively locking said needle holder to said barrel at advanced and retracted positions of the needle holder.

40. The needle-syringe assembly of claim 39 wherein said means for retracting said needle holder is responsive to relative rotational movement between the plunger and the barrel, and said latch means prevents relative rotational movement between the plunger and the barrel.

41. The needle-syringe assembly of claim 39 wherein said plunger forms a longitudinal cavity for receiving said needle holder, and said needle holder includes a member extending laterally from said cavity for engaging said barrel.

42. A needle-syringe assembly, comprising:

an elongated, generally cylindrical barrel forming a hollow nozzle located at the distal end of said barrel and opening into the interior of said barrel;

a plunger slidably mounted in said barrel and forming a longitudinal cavity;

a needle holder carrying a hollow needle on the distal end thereof, said needle holder being slidably mounted in said longitudinal cavity of said plunger, said needle holder including a lateral arm extending laterally through said plunger cavity and engaging said barrel;

guide means extending along a proximal end portion of said barrel for engaging the lateral arm of the needle holder and guiding longitudinal movement of the needle holder within the barrel; and latching means for latching the needle holder to the barrel at advanced and retracted positions of the needle holder relative to the barrel.

43. The needle-syringe assembly of claim 42 wherein said guide means includes a spiral guide surface engaging said lateral arm of the needle holder for moving the needle holder longitudinally relative to the barrel in response to relative rotational movement between the needle holder and the barrel.

44. The needle-syringe assembly of claim 42 wherein said latching means locks the needle holder to the barrel.

45. The needle-syringe assembly of claim 42 wherein said latching means prevents relative movement between the needle holder and the barrel in both the longitudinal and circumferential directions.

46. The needle-syringe assembly of claim 42 wherein said guide means is a spiral slot formed in at least the inside surface of said barrel for receiving an end portion of said lateral arm of the needle holder.

* * * * *